(12) United States Patent
Jahn

(10) Patent No.: US 10,292,796 B2
(45) Date of Patent: May 21, 2019

(54) IMPLANT ANALOG

(71) Applicant: NT-Trading GmbH & Co.KG, Karlsruhe (DE)

(72) Inventor: Dirk Jahn, Weyher (DE)

(73) Assignee: NT-TRADING GMBH & CO. KG, Karlsruhe (DE)

(*) Notice: Subject to any disclaimer, the term of this patent is extended or adjusted under 35 U.S.C. 154(b) by 0 days.

(21) Appl. No.: 14/850,189

(22) Filed: Sep. 10, 2015

(65) Prior Publication Data
US 2015/0374466 A1  Dec. 31, 2015

Related U.S. Application Data

(63) Continuation of application No. PCT/EP2014/054857, filed on Mar. 12, 2014.

(30) Foreign Application Priority Data

Mar. 12, 2013 (DE) .......... 10 2013 102 466
Apr. 29, 2013 (DE) .......... 10 2013 104 352

(51) Int. Cl.
*A61C 8/00* (2006.01)
*A61C 13/34* (2006.01)

(52) U.S. Cl.
CPC .......... *A61C 13/34* (2013.01); *A61C 8/0001* (2013.01); *A61C 8/006* (2013.01); *A61C 8/0045* (2013.01); *A61C 8/0068* (2013.01); *A61C 8/0074* (2013.01); *A61C 8/0089* (2013.01)

(58) Field of Classification Search
CPC ..... A61C 13/34; A61C 8/0001; A61C 8/0045; A61C 8/006; A61C 8/0068; A61C 8/0074; A61C 8/0089

USPC .......... 433/213, 173, 174
See application file for complete search history.

(56) References Cited

U.S. PATENT DOCUMENTS

| | | | | |
|---|---|---|---|---|
| 5,015,186 A * | 5/1991 | Detsch | ........ | A61C 8/0001 433/173 |
| 5,350,297 A * | 9/1994 | Cohen | ........ | A61C 8/0001 433/173 |
| 5,816,809 A * | 10/1998 | Sapkos | ........ | A61C 8/005 433/172 |
| 6,007,336 A * | 12/1999 | Sapkos | ........ | A61C 8/005 433/141 |

(Continued)

FOREIGN PATENT DOCUMENTS

| | | |
|---|---|---|
| EP | 1 704 830 A1 | 9/2006 |
| EP | 2 389 891 A2 | 11/2011 |
| WO | 2009137545 A1 | 11/2009 |

OTHER PUBLICATIONS

Copy of the English translation of the International preliminary report on patentability (Chapter I) for PCT/EP2014/054857 dated Sep. 24, 2015.

*Primary Examiner* — Nicholas D Lucchesi
(74) *Attorney, Agent, or Firm* — Michael Fainberg; Arent Fox LLP

(57) ABSTRACT

The invention relates to a tooth implant analog 10 with an elongated cylindrical body 11, of which the distal end 12 has a connection interface 20 for an abutment and of which the proximal end 16 has an outer thread 28, with an indexing element 22, which is attached to the outer face of the body, and with a depth stop element 18, which is provided on the outer face of the body.

14 Claims, 4 Drawing Sheets

(56) References Cited

U.S. PATENT DOCUMENTS

| | | | | |
|---|---|---|---|---|
| 6,524,106 B1* | 2/2003 | Ziegler | ............... | A61C 8/0001 433/213 |
| 2009/0298015 A1* | 12/2009 | Al-Attar | .............. | A61C 8/0022 433/174 |
| 2011/0262884 A1* | 10/2011 | Zena | ................... | A61C 8/0001 433/201.1 |
| 2014/0272801 A1* | 9/2014 | Ueberuck | ............ | A61C 8/0001 433/213 |

* cited by examiner

IMPLANT ANALOG

BACKGROUND

The present invention relates to a tooth implant analog.

Tooth implant analogs are generally known. They are used, for example, to receive an abutment in a dental model. The tooth implant analog is intended to simulate, in the dental model, the tooth implant introduced into the jawbone of a patient.

Although existing tooth implant analogs have proven useful in practice, there is still some need for improvement, especially in terms of their handling and the precision of their orientation.

Therefore, the object of the present invention is, among others, to make available a tooth implant analog which, for example, allows better handling and provides greater precision of orientation, without making production more difficult.

This object is achieved by a tooth implant analog having the features of claim 1.

SUMMARY OF THE INVENTION

The tooth implant analog according to the present invention comprises an elongated cylindrical body, of which the distal end has a connection interface for an abutment and of which the proximal end has an outer thread, and also an indexing element, which is attached to the outer face of the body, and a depth stop element, which is provided on the outer face of the body.

Further embodiments are set forth in the dependent claims.

BRIEF DESCRIPTION OF DRAWING

It will be appreciated that the aforementioned features and the features still to be explained below can be used not only in the respectively cited combination but also in other combinations or singly, without departing from the scope of the present invention.

Further advantages and embodiments of the invention will become clear from the description and from the accompanying drawing.

The invention is now explained in more detail on the basis of an illustrative embodiment and with reference to the drawings, in which.

DETAILED DESCRIPTION

Figure 1:
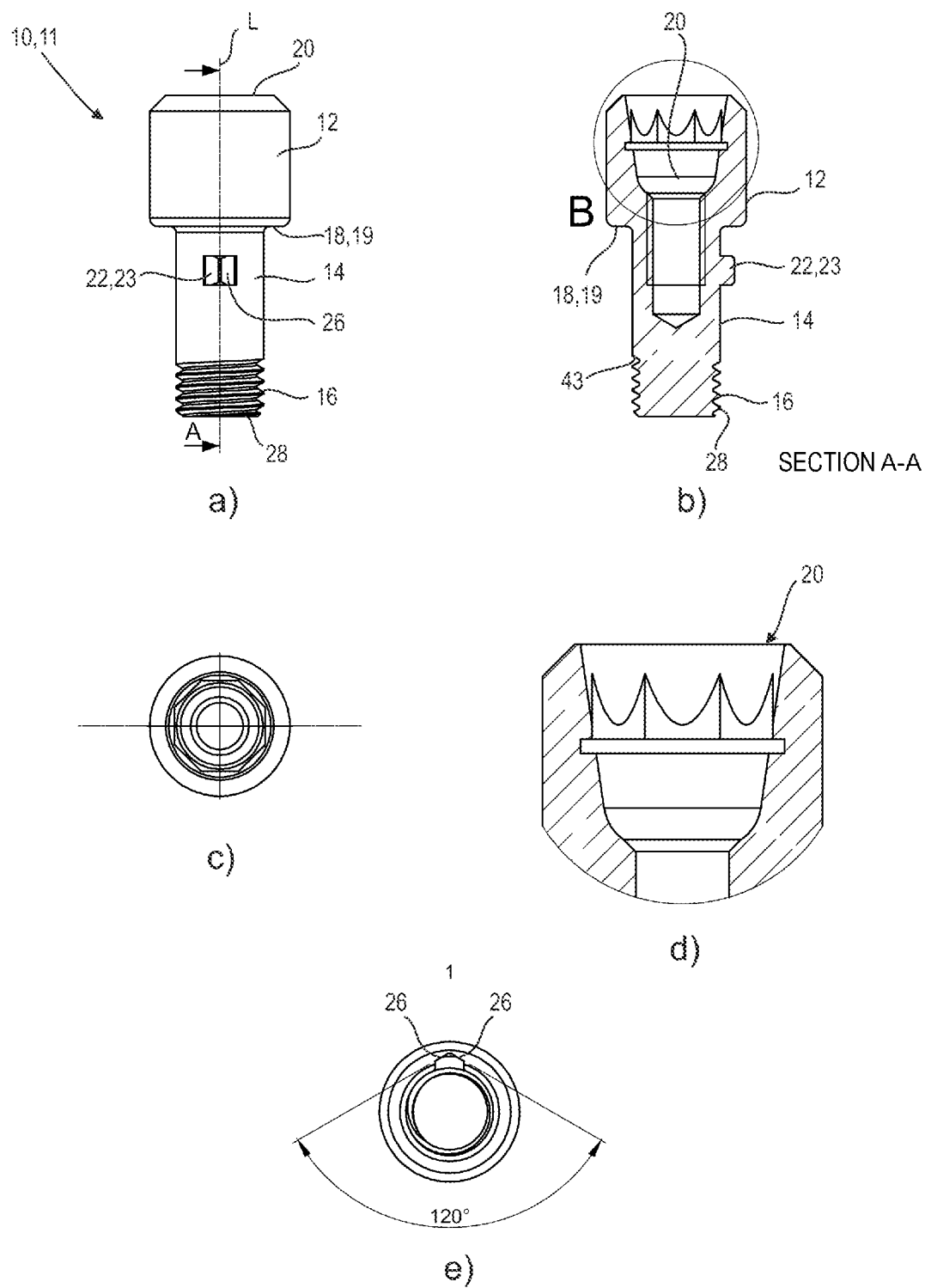
FIG. 1 shows several views of a tooth implant analog according to the present invention.

FIG. 1 shows several views of a tooth implant analog, which is designated by the reference numeral 10. Such a tooth implant analog (hereinafter abbreviated to analog) is provided, for example, for insertion into a dental model. In this model, the analog is intended to simulate a tooth implant of a patient, such that an abutment can be introduced into the analog and can be optically scanned and/or processed in the model.

The analog 10 is designed as an elongated cylindrical body 11, for example of metal. The body 11 is divided into several successive longitudinal portions 12, 14 and 16, wherein the distal longitudinal portion 12 lies at one end of the body 11.

A connection interface 20, which can be seen clearly in FIG. 1b), is provided on the distal longitudinal portion 12. This connection interface is designed depending on a chosen tooth implant/abutment system. That is to say, in other words, the connection interface is adapted to the rotary protection elements and to the tooth implant screw. Since this connection interface can be of any desired configuration, it is not discussed in any more detail here.

The second longitudinal portion 14, adjoining the distal longitudinal portion, has a smaller diameter than the distal longitudinal portion, such that an annular step surface 18 is formed. This step surface 18 preferably extends perpendicular to the longitudinal axis L of the analog 11. The step surface 18 serves as a depth stop element 19.

An indexing element 22 is provided on the second longitudinal portion 14, which has a preferably constant diameter along its longitudinal extent. This indexing element 22 preferably entails several cams 23 which are distributed preferably asymmetrically in the circumferential direction and protrude from the outer surface of the longitudinal portion 14. Three irregularly arranged cams 23 are preferably provided. These cams 23 are intended, on the one hand, to safeguard against rotation and, on the other hand, to permit precise and unambiguous positioning (rotation position) in a dental model.

It will be seen from FIG. 1e) that a cam 23, seen in a plan view, has two surfaces 26 extending outward at an angle of 120° to each other. The cam 23 with the two surfaces 26 is designed to interact with correspondingly designed grooves in the dental model.

The central longitudinal portion is adjoined by the third, proximal longitudinal portion 16, which has an outer thread 28. By way of this outer thread 28, the analog can be secured in the dental model via a fastening nut. The outer thread 28 is assigned a stop which limits the screwing-in path of the fastening nut. The stop consequently ensures a defined position of the fastening nut on the thread, since the fastening nut can only be screwed in as far as this stop.

Figure 2:
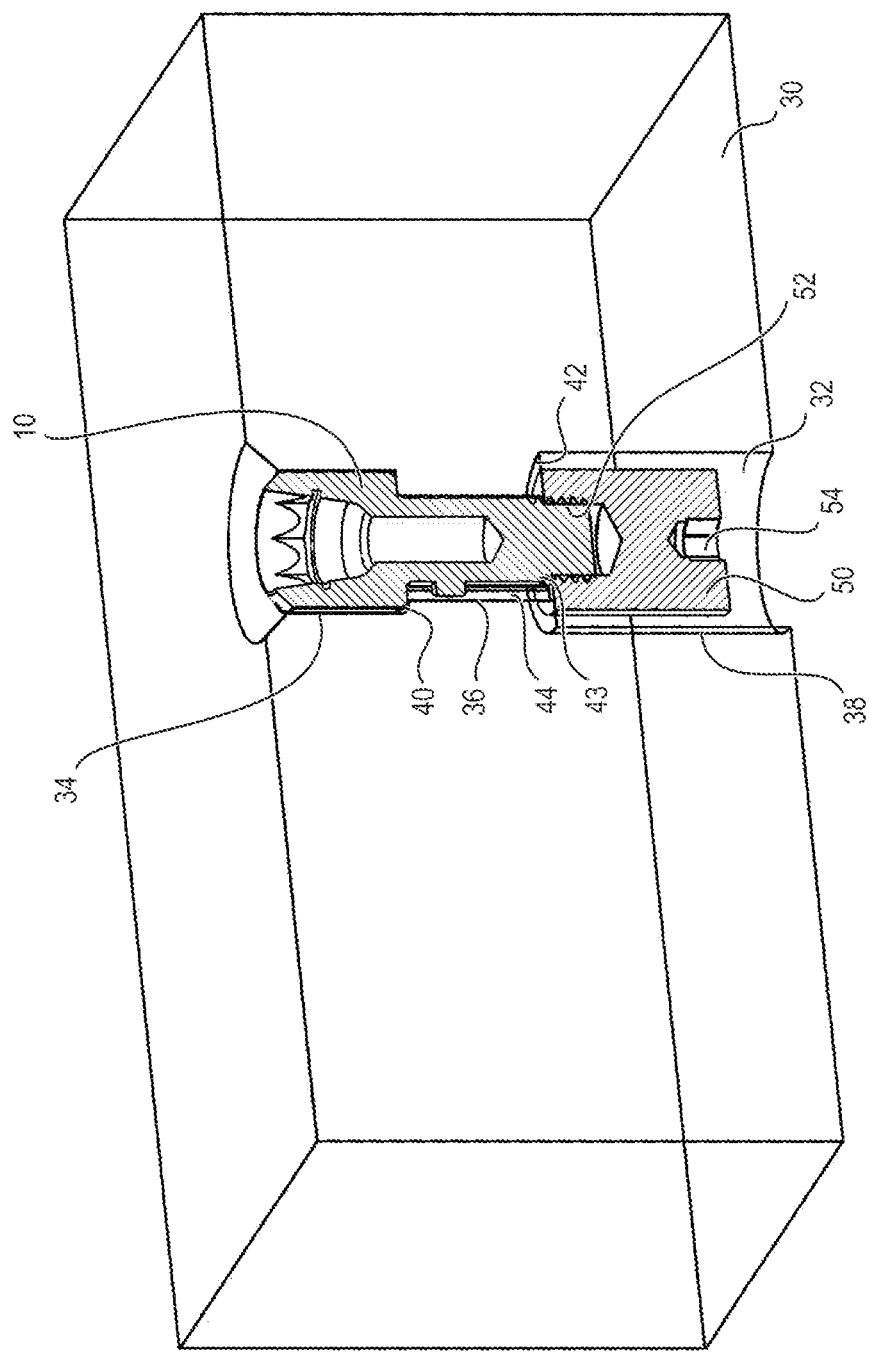
FIG. 2 shows a sectional view of an inserted tooth implant analog.

Such a dental model is now shown schematically in partial section in FIG. 2 and is designated by reference sign 30. A bore 32 for an analog 10 is provided in the dental model 30 and is divided into three longitudinal areas 34, 36 and 38. The first longitudinal area 34, as seen from the top, has a diameter adapted to the external diameter of the distal longitudinal portion 12 of the analog, while the second longitudinal area 36 is adapted to the central longitudinal portion 14. This means that the first longitudinal area 34 has a greater diameter than the second longitudinal area 36, such that a stop surface 40 is formed. The diameter of the second longitudinal area 36 is smaller than the diameter of the third longitudinal area 38, such that a stop surface 42 is formed here too.

Figure 3:
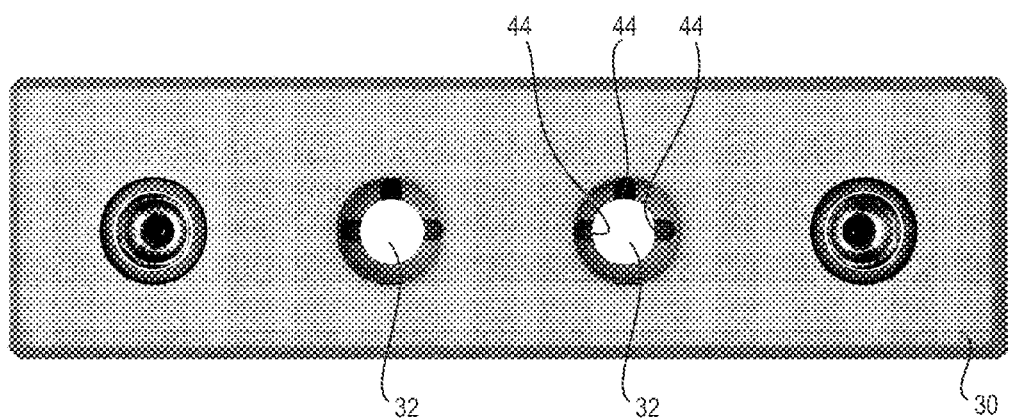
FIG. 3 shows a schematic view of a seat for a tooth implant analog.
Figure 4:
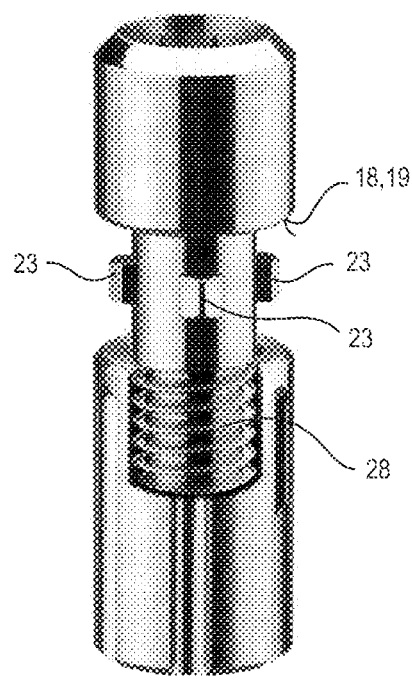
FIG. 4 shows a schematic view of a tooth implant analog with fastening element.

Moreover, in the second longitudinal area 36, a suitably adapted groove 44 is formed for each cam 23, such that unambiguous positioning of the analog in the bore 32 can be ensured. The arrangement and number of the cams 23 is chosen such that the analog can be inserted into the bore 32 only in one rotational position. The three grooves 44 that are provided can be seen clearly in FIG. 3.

Exact positioning in the longitudinal direction L can be ensured via the provided stop surface 40, which interacts with the step surface 18 of the analog 10. The stop surface 40 thus predefines how far the analog 10 can be introduced into the bore 32.

The analog 10 can be secured in the bore 32 by a fastening element 50. The fastening element 50 for this purpose has a bore with an inner thread 52, which is adapted to the outer thread 28 of the analog 10. Moreover, the fastening element 50 has an interface 54 for a tool. This interface is preferably designed to receive a hexagon key.

As will also be seen from FIG. 2, the diameter of the fastening element 50 is greater than the diameter of the second longitudinal area 36 of the bore, such that the fastening element 50 bears on the stop surface 42 when the analog 10 is secured. Moreover, the fastening element bears on the stop 43, which is provided for example on the outer thread. By virtue of the fact that the material of the stop surface 42 is able to yield slightly as the fastening element is screwed in, a stop is also effected on the stop 43 assigned to the outer thread.

To insert the analog 10 into the dental model 30, it is fitted from above into the bore 32, wherein the rotation position has to be chosen such that the cams 23 engage in the corresponding grooves 44. After the cams have engaged in the grooves, a movement in the longitudinal direction is still possible, but a rotation of the analog is no longer possible. As soon as the analog bears on the stop surface 40, the end position of the analog is reached, and, by screwing the fastening element 50 in, the analog is fixed.

The analog 10 in the dental model 30 then allows an abutment to be connected to the analog 10 via the connection interface 20, specifically in a position that corresponds exactly to the position in the oral cavity of a patient.

Figure 5:
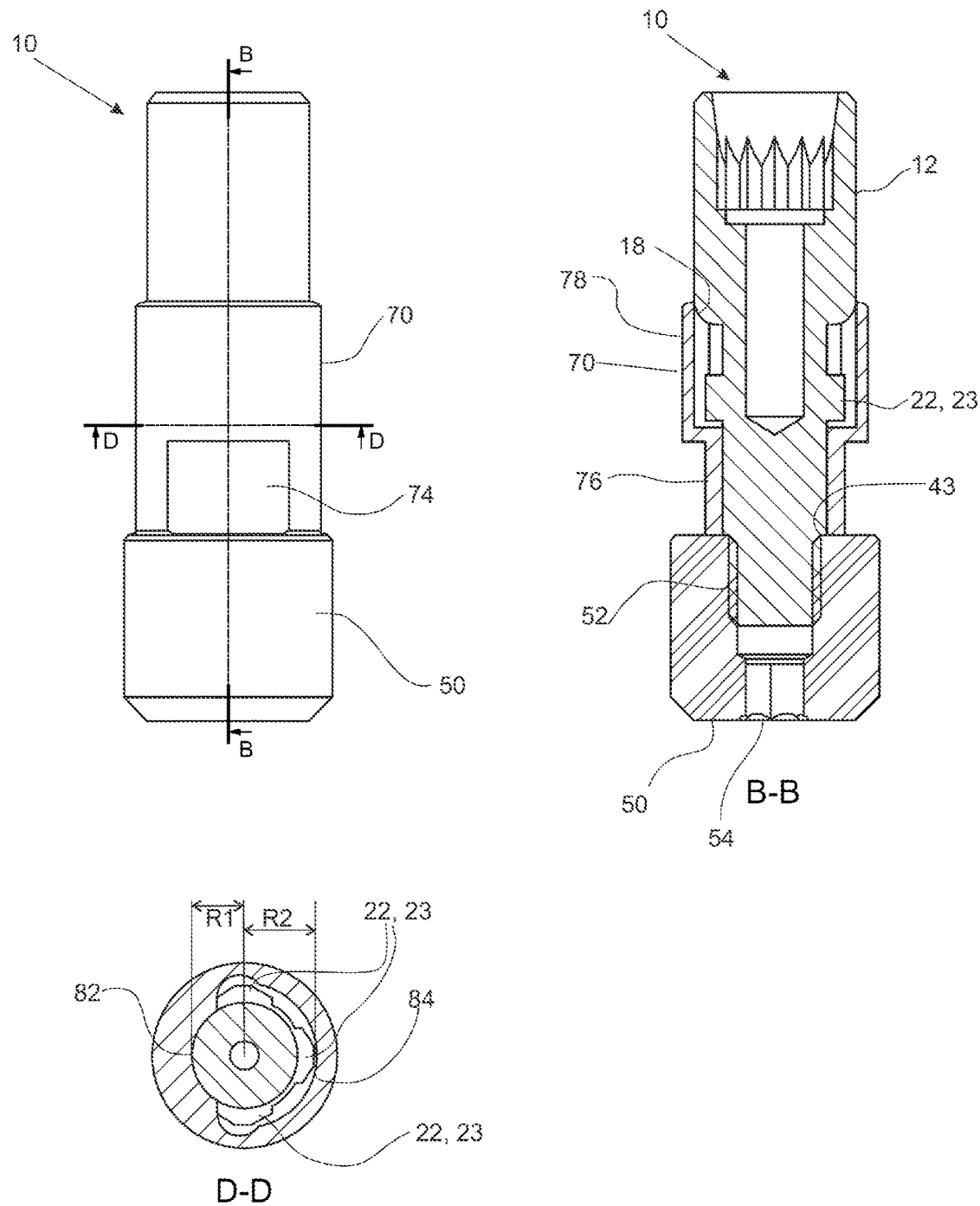
FIG. 5 shows several schematic views of a tooth implant analog with an attached sleeve.

In FIG. 5, the analog 10 already described is shown with a sleeve 70. This sleeve 70 is designed in the shape of a tube and, on the outer surface, has two flattened portions 74 lying opposite each other. These flattened portions 74 are provided in the lower area, i.e. the area directed toward the fastening element 50, and extend in the longitudinal direction to below the center of the sleeve 70. These flattened portions can be used, in a plaster model, for indexing and for protection against rotation.

The length of the sleeve 70 is, for instance, chosen such that it corresponds to the length of the analog 10 from the step surface 18 to the thread 28. In other words, the length of the sleeve 70 corresponds to the length of the second portion 14 of the analog 10.

The interior of the sleeve is divided into two longitudinal portions, namely a lower longitudinal portion 76, which has a substantially circular cross section, and an upper longitudinal portion 78, which has a geometry adapted to the cams 23. In the present example, the cross section in the upper longitudinal portion 78 is made up of two areas 82, 84 with different radii. The radius R1 of the area 82 is smaller than the radius R2 of the other area 84. The smaller radius R1 is adapted to the radius of the outer wall of the analog, while the greater radius is adapted to the radius of the analog in the area of the cams.

The internal geometry of the sleeve 70 in the upper longitudinal portion 78 is therefore designed such that the sleeve can be fitted from below onto the analog 10 preferably only in one predefined rotational position.

This sleeve 70 is used when the analog is used in a plaster model in which there is a danger of the cams 23 becoming surrounded by plaster, in which case a release of the analog would then no longer be possible. Consequently, the sleeve prevents plaster from getting into the area of the cams 23, and it moreover allows the analog 10 to be pulled upward out of the sleeve in the longitudinal direction.

The invention claimed is:

1. A tooth implant analog adapted to receive an abutment and intended to simulate, in a dental model, a tooth implant, wherein the tooth implant analog comprises:
   an elongated cylindrical body, comprising:
   a distal end having an inner connection interface for accepting the abutment into the elongated cylindrical body and
   a proximal end having an outer thread, wherein the connection interface comprises an indexing element as a rotary protection element of the abutment, and wherein the inner connection interface further comprises an inner thread for accepting a screw used for fixing the abutment to the implant analog, and
   wherein the indexing element is attached to an outer face of the body, and the body comprises a depth stop element on the outer face of the body.

2. The tooth implant analog as claimed in claim 1, wherein the indexing element has at least one cam.

3. The tooth implant analog as claimed in claim 1 or 2, wherein the indexing element has three cams, which are distributed in the circumferential direction of the body.

4. The tooth implant analog as claimed in claim 1, wherein the depth stop element is designed as an annular step surface, which extends in the radial direction perpendicular to the longitudinal axis.

5. The tooth implant analog as claimed in claim 4, wherein the step surface is formed by a change of diameter of the body.

6. The tooth implant analog as claimed in claim 1, wherein the indexing element is aligned with respect to an element of the connection interface.

7. The tooth implant analog as claimed in claim 1, comprising a fastening element, which is designed to interact with the outer thread of the body.

8. The tooth implant analog as claimed in claim 7, wherein the fastening element is a fastening nut with an inner thread at one end, in which the inner thread is adapted to the outer thread, and with a screwing-in element at another end.

9. The tooth implant analog as claimed in claim 8, wherein the screwing-in element is designed as an interface for a hexagon socket tool.

10. The tooth implant analog as claimed in claim 1, wherein the connection interface is designed to interact with a dental implant screw and rotary protection elements of the abutment.

11. The tooth implant analog as claimed in claim 1, comprising a sleeve into which the cylindrical body can be fitted at least in part.

12. The tooth implant analog as claimed in claim 11, wherein, on its inner face, the sleeve has a geometry which, together with the indexing element, provides indexing and protection against rotation.

13. The tooth implant analog as claimed in claim 11, wherein, on its outer face, the sleeve has at least one flattened portion.

14. A tooth implant analog adapted to receive an abutment and intended to simulate, in a dental model, a tooth implant, the tooth implant analog comprising:
   an elongated cylindrical body comprising a first distal longitudinal section, a second middle longitudinal section and a third proximal longitudinal section, the first distal longitudinal section having an inner connection interface for the abutment, the third longitudinal section having an outer thread, and the second middle longitudinal section having a constant diameter along its length, wherein the inner connection interface comprises an indexing element as a rotary protection element of the abutment, and wherein the inner connection interface comprises an inner thread for accepting a screw used for fixing the abutment to the implant analog, wherein the indexing element is attached to the outer face of the body at the second middle longitudinal section, and wherein the implant analog comprises a depth stop element, which is provided on the outer face of the body at the first distal longitudinal section and configured to define an annular step surface extending in radial direction perpendicular to a longitudinal axis of the body, wherein the step surface is formed by a change of diameter of the body from the first distal longitudinal section to the second middle longitudinal section, a fastening element configured to engage with the outer thread of the body, and a stop assigned to the outer thread and limiting the screwing-in path of the fastening element.

* * * * *